(12) United States Patent
Pan et al.

(10) Patent No.: US 11,313,989 B2
(45) Date of Patent: Apr. 26, 2022

(54) DETECTING DEVICE

(71) Applicant: National Central University, Taoyuan (TW)

(72) Inventors: Min-Chun Pan, Taoyuan (TW);
Wei-Hao Lee, New Taipei (TW);
Po-Chin Chang, Taipei (TW);
Tsung-Hsuan Su, Tainan (TW)

(73) Assignee: National Central University, Taoyuan (TW)

( * ) Notice: Subject to any disclaimer, the term of this patent is extended or adjusted under 35 U.S.C. 154(b) by 164 days.

(21) Appl. No.: 16/941,513

(22) Filed: Jul. 28, 2020

(65) Prior Publication Data
US 2021/0157023 A1    May 27, 2021

(30) Foreign Application Priority Data

Nov. 27, 2019   (TW) .................................. 108143258

(51) Int. Cl.
*G01V 3/08* (2006.01)
*G01V 3/165* (2006.01)
(Continued)

(52) U.S. Cl.
CPC .................. *G01V 3/08* (2013.01); *A61B 5/05* (2013.01); *A61B 5/4851* (2013.01); *G01V 3/165* (2013.01); *A61B 2562/0223* (2013.01)

(58) Field of Classification Search
CPC .......... G01V 3/08; G01V 3/165; G01V 3/081; A61B 5/05; A61B 5/4851;
(Continued)

(56) References Cited

U.S. PATENT DOCUMENTS

| 8,391,958 B2 | 3/2013 | Cawley et al. |
| 2011/0200965 A1 | 8/2011 | Petersson et al. |

(Continued)

FOREIGN PATENT DOCUMENTS

| DE | 102006051032 A1 | 4/2008 |
| TW | 200916059 A | 4/2009 |

(Continued)

OTHER PUBLICATIONS

M. Yamane et al., "Measuring tooth mobility with a no-contact vibration device," Journal of Periodontal Research, 2008, vol. 43, pp. 84-89.

(Continued)

*Primary Examiner* — Giovanni Astacio-Oquendo
(74) *Attorney, Agent, or Firm* — CKC & Partners Co., LLC

(57) ABSTRACT

The present disclosure is related to a detecting device which includes a fixing component, a sensing component, and a terminal. The fixing component is fixed to an object under test and generates a first magnetic field. The sensing component includes a driving module and a reference module. The driving module generates a second magnetic field, and the driving module further generates a sensing signal according to an electromagnetic induction produced by the first magnetic field and the second magnetic field. The reference module is spaced from the driving module by a distance, such that the reference module is outside of the second magnetic field and generates a reference signal. The terminal produces detection information according to the sensing signal and the reference signal.

10 Claims, 3 Drawing Sheets

(51) Int. Cl.
  *A61B 5/05* (2021.01)
  *A61B 5/00* (2006.01)
(58) Field of Classification Search
  CPC ............ A61B 2562/0223; A61B 5/062; A61B 5/6897; A61B 5/6898
  USPC ................................ 324/207.11, 200, 207.12
  See application file for complete search history.

(56) References Cited

U.S. PATENT DOCUMENTS

| | | |
|---|---|---|
| 2013/0078596 A1 | 3/2013 | Pan et al. |
| 2014/0072929 A1 | 3/2014 | Cawley et al. |
| 2014/0199650 A1 | 7/2014 | Moffson et al. |
| 2015/0105630 A1* | 4/2015 | Kummerl ............ A61B 5/02438 600/502 |
| 2015/0150474 A1* | 6/2015 | Pan ...................... A61B 5/4547 433/173 |
| 2019/0162606 A1 | 5/2019 | Puttlitz et al. |
| 2022/0043499 A1* | 2/2022 | Wei ........................... G06F 1/28 |

FOREIGN PATENT DOCUMENTS

| | | |
|---|---|---|
| TW | I389675 B | 3/2013 |
| TW | 201521687 A | 6/2015 |
| TW | I617292 B | 3/2018 |
| WO | 2016/204684 A1 | 12/2016 |

OTHER PUBLICATIONS

Chia, T. S. et al., "Assessment of Dental Implantation Osseointegration Through Electromagnetic Actuation and Detection," Journal of Medical Devices, Sep. 2014, vol. 8.

* cited by examiner

DETECTING DEVICE

CROSS-REFERENCE TO RELATED APPLICATION

This application claims priority to Taiwan Application Serial Number 108143258, filed Nov. 27, 2019, which is herein incorporated by reference.

BACKGROUND

Field of Invention

The present invention relates to a detecting device. More particularly, the present invention relates to a magnetic detecting device.

Description of Related Art

In the manufacturing and medical fields, detection of the connection elements, fixing elements, and implants is an important aspect. The connection elements and fixing elements can be replaced before being broken if the conditions thereof are well detected. In this way, a machine equipped with the proper connection elements or fixing elements can avoid malfunction.

In the medical field, a process of integrating an implant with a bone is time-consuming, and every stage of the process must be recorded and evaluated. Physicians need to observe patients' implants to comprehensively understand their post-operative conditions. Therefore, in order to acquire information regarding these bone implants, a well-designed detecting device is necessary.

In some circumstances, the volume and the sensitivity of the detection device are quite critical. Taking dental implants as an example, the amount of space within and in the vicinity of a human mouth is limited, and for this purpose, the creation of a sensitive detecting device for the detection of tooth implants, but also containing a small volume has become more and more important. Another point for consideration is, in the medical field, it is also quite necessary to provide a non-contact detection device to prevent the bacteria and viruses from spreading in consideration of hygiene.

In conclusion, there is a need for the development of a detecting device which can solve the aforementioned problems of volume and sensitivity.

SUMMARY

One aspect of the present disclosure is related to a detecting device which includes a fixing component, a sensing component, and a terminal. The fixing component is fixed to an object under test and generates a first magnetic field. The sensing component includes a driving module and a reference module. The driving module generates a second magnetic field, and the driving module further generates a sensing signal according to an electromagnetic induction produced by the first magnetic field and the second magnetic field. The reference module is spaced from the driving module by a distance, such that the reference module is outside of the second magnetic field and generates a reference signal. The terminal produces detection information according to the sensing signal and the reference signal.

In some embodiments of the present disclosure, the driving module includes a first magnetic unit and a first sensing unit. The first magnetic unit generates the second magnetic field. The first sensing unit generates the sensing signal according to the electromagnetic induction.

In some embodiments of the present disclosure, the distance between the reference module and the driving module is equal to or greater than six times the length of the first magnetic unit.

In some embodiments of the present disclosure, the distance between the reference module and the driving module can be determined according to relation (1). The relation (1) is $$\frac{1}{x^2} + \frac{1}{(x+2L)^2} \cong \frac{2}{(x+L)^2}$$

in which L represents the length of the first magnetic unit and x represents the distance.

In some embodiments of the present disclosure, the first sensing unit is located between the first magnetic unit and the reference module.

In some embodiments of the present disclosure, the reference module includes a second magnetic unit and a second sensing unit. The second magnetic unit generates a third magnetic field. The second sensing unit generates a reference signal according to the third magnetic field.

In some embodiments of the present disclosure, the second magnetic field and the third magnetic field are identical alternating magnetic fields.

In some embodiments of the present disclosure, the first sensing unit and the second sensing unit are magnetic sensors.

In some embodiments of the present disclosure, the fixing component is ring-shaped or stick-shaped.

In some embodiments of the present disclosure, the sensing component includes a transmission unit, and the terminal includes a receiving unit.

In conclusion, the present disclosure provides a detecting device which generates a sensing signal according to an electromagnetic induction produced by a first magnetic field and a second magnetic field. Thereafter, defective situations of an implant or a machine part can be obtained, by comparing the sensing signal with a reference signal. A driving module and a reference module of the detecting device are spaced apart by a distance, such that the reference module can be outside of a second magnetic field of the driving module. Therefore, the reference signal of the reference module is not affected by the second magnetic field, and thus detection results thereof are accurate.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
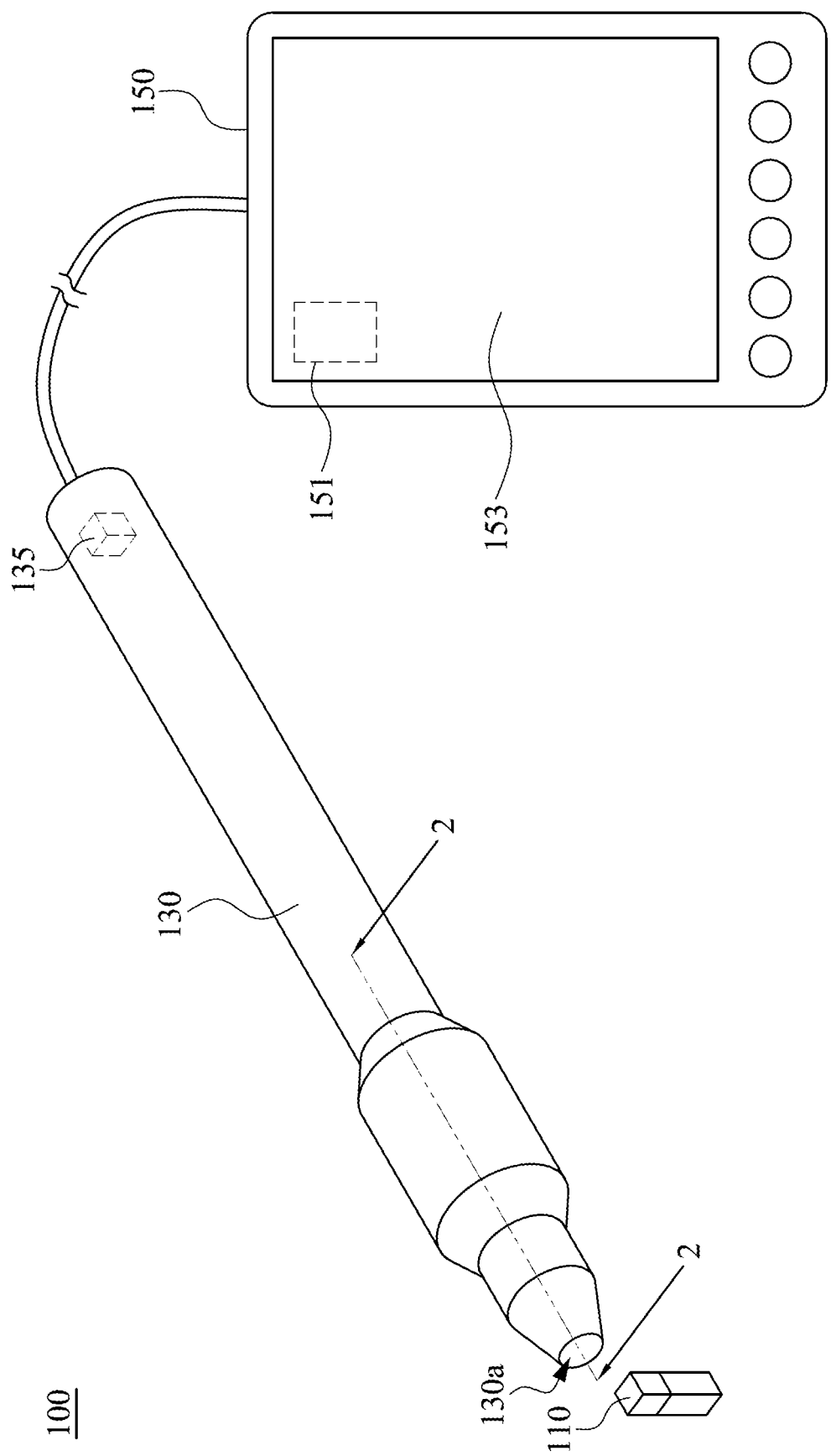
FIG. 1 schematically depicts a perspective view of a sensing device in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the some embodiments and/or configurations discussed.

The terms used in this specification generally have their ordinary meanings in the art and in the specific context where each term is used. The use of examples in this specification, including examples of any terms discussed herein, is illustrative only, and in no way limits the scope and meaning of the disclosure or of any exemplified term. Likewise, the present disclosure is not limited to some embodiments given in this specification.

Although the terms "first," "second," etc., may be used herein to describe various elements, these elements should not be limited by these terms. These terms are used to distinguish one element from another. For example, a first element could be termed a second element, and, similarly, a second element could be termed a first element, without departing from the scope of the embodiments. As used herein, the term "and/or" includes any and all combinations of one or more of the associated listed items.

The terms "comprise," "comprising," "include," "including," "has," "having," etc. used in this specification are open-ended and mean "comprises but not limited to."

Figure 2:
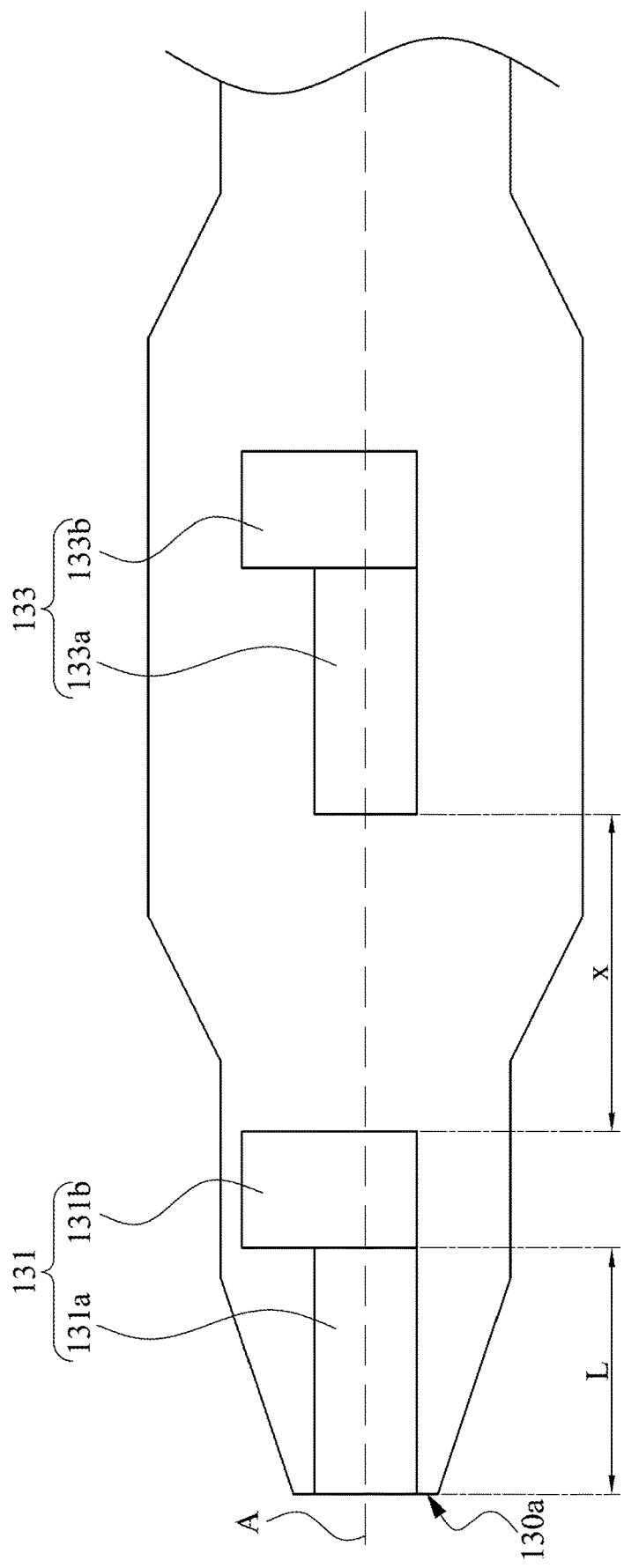
FIG. 2 is a schematic cross-sectional view of the sensing device taken along the line 2-2 in the FIG. 1.

Please refer to FIG. 1 and FIG. 2. FIG. 1 schematically depicts a perspective view of a detecting device 100 in accordance with some embodiments of the present disclosure. FIG. 2 is a schematic cross-sectional view of the detecting device 100 taken along the line 2-2 in the FIG. 1. In an embodiment of the present disclosure, a detecting device 100 includes a fixing component 110, a sensing component 130, and a terminal 150. The fixing component 110 can be fixed to an object under test and generate a first magnetic field. The sensing component 130 includes a driving module 131 and a reference module 133. The driving module 131 generates a second magnetic field, and the driving module 131 further generates a sensing signal according to an electromagnetic induction produced by the first magnetic field and the second magnetic field. The reference module 133 is spaced from the driving module 131 by a distance x, such that the reference module 133 is located outside of the second magnetic field and generates a reference signal. Thereafter, the terminal 150 produces detection information by comparing the sensing signal with the reference signal.

Specifically, the fixing component 110 can be fixed to an object under test and generate a first magnetic field. When the first magnetic field is in the range of the second magnetic field which is generated by the driving module 131, the first magnetic field interacts with the second magnetic field to produce attractive forces and repulsive forces to vibrate the object under test. The second magnetic field is an alternating magnetic field, and thus the intensity and polarity of the second magnetic field changes with time. The first magnetic field also interacts with the second magnetic field to produce electromagnetic induction. The driving module 131 generates sensing signal according to the electromagnetic induction. Therefore, the terminal 150 can produce detection information about the object under test in accordance with the sensing signal and the reference signal.

The driving module 131 is spaced from the reference module 133 by a distance x to be located outside of the second magnetic field, such that the reference module is not affected by the second magnetic field. That is to say, the reference module 133 is located at a position where the magnetic lines of the second magnetic field do not pass through. The above mentioned configuration can prevent the reference module 133 from being interfered by the second magnetic field, and thus the terminal 150 can generate more accurate detection information about vibration condition of the object under test.

Reference is made to FIG. 2. In an embodiment of the present disclosure, the driving module 131 includes a first magnetic unit 131a and a first sensing unit 131b. The first magnetic unit 131a generates the second magnetic field. The first sensing unit 131b generates the sensing signal according to the electromagnetic induction which is produced by the first magnetic field and the second magnetic field. The first sensing unit 131b is located at a position where the magnetic lines of the second magnetic field pass through to sense the electromagnetic induction and generate the sensing signal.

Specifically, the distance x between the driving module 131 and the reference module 133 is equal to or greater than six times a length L of the first magnetic unit. The distance x between the driving module 131 and the reference module 133 is measured along with an axis A shown in FIG. 2. The first magnetic unit 131a is also measured along with the axis A to acquire the length L.

The distance x is at least six times the length L of the first magnetic unit, such that the reference module 133 can be located outside of the second magnetic field. Since the shortest distance x to avoid the second magnetic field from interfering is six times the length L, the detecting device 100 can be minimized and produce accurate detection information by using a first magnetic unit 131a with the shortest length L. Such relation can be obtained by a formula (1):

$$f(x) \cong \frac{\pi\mu}{4} M^2 R^2 \left[ \frac{1}{x^2} + \frac{1}{(x+2L)^2} - \frac{2}{(x+L)^2} \right],$$

and the relevant detail information and clarification thereof are described in paragraphs thereafter.

Reference is made to FIG. 2. In an embodiment of the present disclosure, the first sensing unit 131b is located between the first magnetic unit 131a and the reference module 133. In such configuration, the first magnetic unit 131a is closer to a detecting end 130a of the sensing component 130 than the first sensing unit 131b, and thus the first magnetic unit 131a is closer to the first magnetic field of the fixing component in order to produce stronger electromagnetic induction. The first sensing unit 131b can generate more accurate sensing signal according to the stronger electromagnetic induction. The detecting end 130a refers to an end of the sensing component 130 which is used to get close to the object under test for detecting it.

In some embodiments of the present disclosure, the reference module 133 includes a second magnetic unit 133a and a second sensing unit 133b. The second magnetic unit 133a generates a third magnetic field. The second sensing unit 133b senses the third magnetic field to generate a reference signal.

Specifically, the second sensing unit 133b of the reference module 133 is located outside of the second magnetic field which means the second sensing unit 133b is located at a position where magnetic lines of the second magnetic field do not pass through. Since the second magnetic unit 133a is between the second sensing unit 133b and the driving module 131, the second sensing unit 133b is farther away from the driving module 131 than the second magnetic unit 133a. In this case, the second magnetic field affects the second sensing unit 133b less, and this configuration can help to make the size of the sensing component 130 down.

In some embodiments of the present disclosure, the second magnetic field and the third magnetic field are two identical alternating magnetic fields. Furthermore, frequencies of the second magnetic field and the third magnetic field are from about 200 Hz to about 10,000 Hz. Defective information about the object under test can be inferred by comparing a reference signal of the third magnetic field with a sensing signal from the electromagnetic induction which is produced by the first magnetic field and the second magnetic field.

In some embodiments of the present disclosure, the two identical maximum magnetic fields of the first magnetic unit 131a and the second magnetic unit 133a can be converted into two identical equivalent cylindrical magnets mathematically. Lengths of the two equivalent cylindrical magnetics are substantially the same as the lengths of the first magnetic unit 131a and second magnetic units 133a, and thus lengths of the equivalent cylindrical magnets can be assumed as lengths L. In some cases, a gauss meter can be used to measure a magnetic field so as to obtain a corresponding equivalent cylindrical magnetic. In accordance with the formula (1):

$$f(x) \cong \frac{\pi \mu}{4} M^2 R^2 \left[ \frac{1}{x^2} + \frac{1}{(x+2L)^2} - \frac{2}{(x+L)^2} \right],$$

and the two identical equivalent cylindrical magnetics, the minimum distance between the driving module 131 and the reference module 133 can be obtained in which f(x) represents a force between magnetics, p represents vacuum permeability of two magnetics, M is magnetization of two magnetics, R represents radiuses of two magnetics, L represents lengths of two magnetics and X2 represents a distance between two magnetics. When the forces between two magnetics are substantially equal to zero (f(x) is equal to zero), the distance between two magnetics is a minimum distance X2. As can be known by calculating the formula (1), when f(x) is equal to zero, the minimum distance X2 between of the two equivalent cylindrical magnetics is solely decided by the length L. Therefore, decreasing the length L of the first magnetic unit 131a can minimize the detecting device 100 and prevent the second magnetic field from interfering.

Specifically, if the forces between the two magnets are equal to zero, the second magnetic field and the third magnetic field does not interact. That is, reference module 133 is not affected by the second magnetic field. While the f(x) of the formula (1) is equal to zero, the aforementioned vacuum permeability p, the magnetization M, and the radius R shall be neglected. Therefore, the minimum distance X2 between the two magnets is equal to six times the length L of the first magnetic unit 131a. Since the length of the first magnetic unit 131a and the lengths of the equivalent cylindrical magnetics are the same, the minimum distance X2 is equal to the minimum distance x between the driving module 131 and the reference module 133, and thus relation (1):

$$\frac{1}{x^2} + \frac{1}{(x+2L)^2} \cong \frac{2}{(x+L)^2}$$

is acquired. According to the above mentioned information, when the distance x is at least equal to six times the length L of the first magnetic unit 131a, the driving module 131 does not affect the reference module 133. In conclusion, the length L of the first magnetic units 131a is one of the most critical factors related to the size of sensing component 130, and decreasing the length L can make the size of the sensing component 130 down and avoids the reference module 133 from being interfering by the second magnetic field.

In some embodiments of the present disclosure, the first sensing unit 131b and the second sensing unit 133b are magnetic sensors such as Hall Effect Sensors, but the present disclosure is not limited in this respect. The Hall Effect sensors can produce electrical potential differences within a magnetic field. In contrast, the Hall Effect sensors do not produce electrical potential differences, as being outside of a magnetic field.

In some embodiments of the present disclosure, the first magnetic unit 131a and the second magnetic unit 133a are inducers, such as wire wound inductors, laminated inductors, and thin film inductors, but the present disclosure is not limited in this respect.

In some embodiments of the present disclosure, the fixing component 110 is a ring-shaped magnet or a stick-shaped magnet. The shape and size of the fixing component 110 are determined by the object under test itself or the best way to show osseointegration stability between a bone structure and the object under test such as a bone implant, and the present disclosure is not limited in this respect.

Figure 3B:
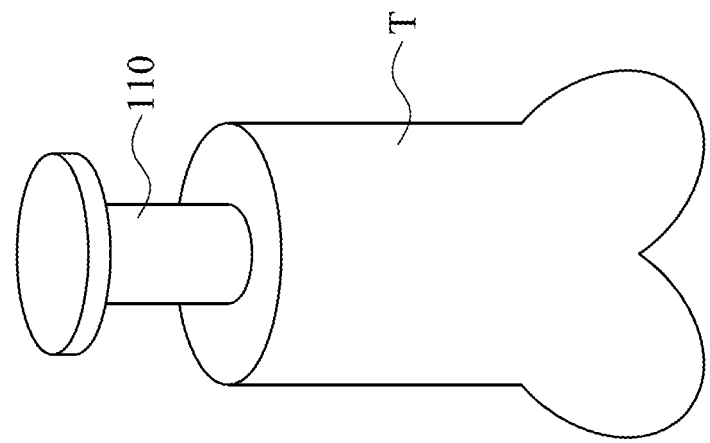
FIG. 3B schematically depicts a perspective view of a fixing component in FIG. 1 in accordance with another embodiment of the present disclosure.
Figure 3A:
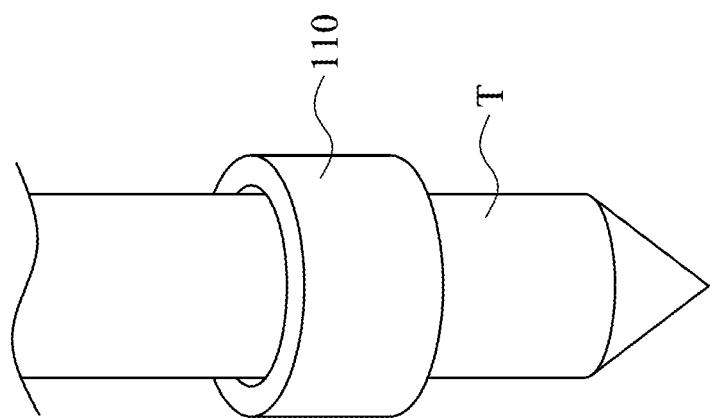
FIG. 3A schematically depicts a perspective view of a fixing component in FIG. 1 in accordance with an embodiment of the present disclosure.

Reference is made to FIG. 3A. While the fixing component 110 is a ring-shaped magnet, it can be applied to an object under test T which is a machine part. The inside diameter of the fixing component 110 can be decided depending on the size or category of the machine part.

Reference is made to FIG. 3B. While the fixing component 110 is a stick-shaped magnet, it can be applied to an object under test T which is a human bone or an implant. The size of the fixing component 110 can be adjusted based on the size and the category of the human bone or implant. If a detected human bone is a shinbone or a collar bone, the fixing component 110 is larger to fit. If a detected human bone is a tooth, the fixing component 110 is in a small size. The detecting device 100 can be used in various fields, and the size and the shape of the fixing component 110 are decided based on the object under test T in order to detect the defective situation thereof. In some other embodiments of the present disclosure, the fixing component 110 can be a pin-shaped magnet, but the present disclosure is not limited in this respect.

Reference is made to FIG. 1. In some embodiments of the present disclosure, the sensing component 130 includes a transmission unit 135. The terminal 150 includes a receiving unit 151 (the transmission unit 135 and the receiving unit 151 shown in dotted lines are respectively located inside the sensing component 130 and the terminal 150). Through the transmission unit 135 and the receiving unit 151, some necessary elements can be located outside of the sensing component 130. For instance, processing hardware and display panels can be outside of the sensing component 130, such that the volume of the sensing component 130 can decrease and still maintain its functions. The transmission unit 135 and the receiving unit 151 can adopt wire connection or wireless connection to fulfill signal transmission and signal receiving. Specifically, the wireless connection can be fulfilled by wireless connection techniques, such as Wi-Fi, Bluetooth, or ZigBee. The present disclosure is not limited in this respect.

In some embodiments of the present disclosure, the terminal 150 is a computing device, such as a desktop computer, a notebook computer, a tablet computer, or a smart phone, and the present disclosure is not limited in this respect. The category of the terminal 150 can be decided by a user's requirements.

In some embodiments of the present disclosure, the terminal 150 includes a display unit 153 for showing the information about the object under test T. The display unit 153 can include a light-emitting diode (LED) display panel or an organic light-emitting diode (OLED) display panel, but the present disclosure is not limited in this respect.

In conclusion, the present disclosure provides a detecting device which generates a sensing signal according to an electromagnetic induction produced by a first magnetic field and a second magnetic field. Thereafter, defective situations of an implant or a machine part can be obtained, by comparing the sensing signal with a reference signal. A driving module and a reference module of the detecting device are spaced apart by a distance, such that the reference module can be outside of a second magnetic field of the driving module. Therefore, the reference signal of the reference module is not affected by the second magnetic field, and thus detection results thereof are accurate.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A detecting device comprising:
    a fixing component configured to be fixed to an object under test and generate a first magnetic field;
    a sensing component comprising:
        a driving module generating a second magnetic field, and the driving module further generates a sensing signal according to an electromagnetic induction produced by the first magnetic field and the second magnetic field; and
        a reference module spaced from the driving module by a distance, such that the reference module is outside of the second magnetic field and configured to generate a reference signal; and
    a terminal configured to produce detection information according to the sensing signal and the reference signal.

2. The detecting device of claim 1, wherein the driving module comprises:
    a first magnetic unit configured to generate the second magnetic field; and
    a first sensing unit configured to generate the sensing signal according to the electromagnetic induction.

3. The detecting device of claim 2, wherein the distance is equal to or greater than six times a length of the first magnetic unit.

4. The detecting device of claim 3, wherein the distance is determined according to a relation (1), the relation (1) is $$\frac{1}{x^2} + \frac{1}{(x+2L)^2} \cong \frac{2}{(x+L)^2},$$

and L represents the length of the first magnetic unit and x represents the distance.

5. The detecting device of claim 2, wherein the first sensing unit is between the first magnetic unit and the reference module.

6. The detecting device of claim 2, wherein the reference module comprises:
    a second magnetic unit configured to generate a third magnetic field; and
    a second sensing unit configured to generate a reference signal according to the third magnetic field.

7. The detecting device of claim 6, wherein the second magnetic field and the third magnetic field are identical alternating magnetic fields.

8. The detecting device of claim 6, wherein the first sensing unit and the second sensing unit are magnetic sensors.

9. The detecting device of claim 1, wherein the fixing component is ring-shaped or stick-shaped.

10. The detecting device of claim 1, wherein the sensing component further comprises a transmission unit, and the terminal comprises a receiving unit.

* * * * *